United States Patent [19]

Sköld

[11] Patent Number: 5,523,431
[45] Date of Patent: Jun. 4, 1996

[54] METHOD OF PRODUCING AN AMIDE PRODUCT MIXTURE, AN AMIDE PRODUCT MIXTURE AND THE USE THEREOF

[75] Inventor: Rolf Sköld, Stenungsund, Sweden

[73] Assignees: Berol Nobel AB, Stenungsund, Sweden; Castrol Ltd., Wiltshire, United Kingdom

[21] Appl. No.: 140,059

[22] PCT Filed: Apr. 29, 1992

[86] PCT No.: PCT/SE92/00280

§ 371 Date: Oct. 29, 1993

§ 102(e) Date: Oct. 29, 1993

[87] PCT Pub. No.: WO92/19587

PCT Pub. Date: Nov. 12, 1992

[30] Foreign Application Priority Data

May 2, 1991 [SE] Sweden ................... 9101312

[51] Int. Cl.$^6$ ................................. C07C 231/00
[52] U.S. Cl. ................. 554/70; 554/66; 554/68; 554/69; 554/149
[58] Field of Search ................. 854/66, 68, 69, 854/70, 149; 252/525, 2.5 R; 424/20

[56] References Cited

U.S. PATENT DOCUMENTS 2,429,445  10/1947  Young et al. ............... 554/66

FOREIGN PATENT DOCUMENTS 0381548  8/1990  European Pat. Off. .
386826   9/1990  European Pat. Off. .
1140867  1/1969  United Kingdom .
9219587  11/1992 WIPO .

OTHER PUBLICATIONS

PCT–International Preliminary Examination Report, Jul. 15, 1993.

Primary Examiner—José G. Dees
Assistant Examiner—Deborah D. Carr
Attorney, Agent, or Firm—Spencer & Frank

[57] ABSTRACT

The present application relates to a method of producing an amide product mixture having a low content of secondary amines by reacting an amide product mixture having a high secondary amine content with an aliphatic alkylene oxide in the absence of an essential amount of any alkoxylation catalyst. The amide product mixture obtained contains a minor amount of tertiary amines and exhibits advantageous properties when used for the formulation of cosmetic products, such as shampoos and creams; foam cleaning compositions, e.g. for textiles and cars; and functional fluids, such as lubricants, metal working fluids and hydraulic fluids.

8 Claims, No Drawings

METHOD OF PRODUCING AN AMIDE PRODUCT MIXTURE, AN AMIDE PRODUCT MIXTURE AND THE USE THEREOF

This application is 371 of PCT/SE92/00200 filed Apr. 29, 1992.

BACKGROUND OF THE INVENTION

1. Field of the Invention

The present application relates to a method of producing an amide product mixture having a low content of secondary amines. The amide product mixture obtained contains a minor amount of tertiary amines and exhibits advantageous properties when used for the formulation of cosmetic products, such as shampoos and creams; foam cleaning compositions, e.g., for textiles and cars; and functional fluids, such as lubricants, metal working fluids and hydraulic fluids.

2. Description of the Related Art

The use of amides manufactured by amidation of monocarboxylic acids or their alkylesters, such as methyl esters, with secondary amines, such as diethanolamine, in a variety of cosmetic products, foam cleaning compositions and industrial fluids, is well known. In order to avoid the formation of undesired by-products, such as monoesters, diesters, and different types of esteramides, the amidation reaction has normally been carried out in a surplus of the secondary amine, such as diethanolamine, which, after the reaction, is present unreacted in the reaction mixture. The content of the secondary amine in the reaction mixture may vary within wide limits, but will be above 1% by weight. Where the reactants are a monocarboxylic acid and diethanolamine, the content of secondary amine is normally between 10% and 30% by weight and with the metylester of a monocarboxylic acid and diethanolamine as reactants, the content of secondary amine will be about 5–10% by weight.

The fact that the amide product mixture contains a large amount of secondary amine, such as diethanolamine, has not been considered as any real drawback as the secondary amine has contributed to improved anticorrosion properties when used in functional fluids and to a desired alkalinity and foam stabilization when used in cosmetic products and foam cleaning compositions.

Recently, more attention has been paid to the fact that secondary amines, such as diethanolamine, are toxic and form nitrosamines, which are carcinogenic in animal tests. Therefore, a reduction of the content of secondary amines is desirable. The content should, according to recommendations, be less than 1% by weight.

Thus, one object of the present invention is to produce an amide product mixture which contains secondary amines containing less than 1% by weight.

Another object of the invention is that the method of producing the amide product mixture shall be simple to perform and that the amide product mixture shall be useable without any additional cleaning and/or working-up processes.

Another object of the invention is to keep the formation of esters, diesters and esteramides to a low level.

Still another object of the invention is that the amide product mixture shall at least have about the same corrosion inhibiting ability and/or defoaming properties in functional fluids and at least about the same foam stabilizing properties in cosmetics and foam cleaning products as the corresponding amide product mixture with high contents of secondary amines.

SUMMARY OF THE INVENTION

According to the invention it has been found that these objects can be met by producing an amide product mixture containing a major part of a monocarboxylic acid amide having the formula

where R is an aliphatic hydrocarbon group having 7–23 carbon atoms, $R_1$ and $R_2$ are, independent of each other, an alkyl group having 2–8 carbon atoms, perferably 1–4 carbon atoms or hydroxylalkyl groups having 2–8 carbon atoms, preferably 2–4 carbon atoms; and less than 1% by weight of a secondary amine having the formula

where $R_1$ and $R_2$ have the meaning mentioned above; from an amide product mixture containing a major part of a monocarboxylic acid amide having the formula (I) and more than 1% by weight of a secondary amine having the formula (II) characterised in that the amine product mixture containing more than 1% by weight of the secondary amine II is alkoxylated with an aliphatic alkylene oxide having 2–8 carbon atoms, preferably 2–4 carbon atoms in the absence of an essential amount of any alkoxylation catalyst, until the content of the secondary amine is less than 1% by weight. By the expression "major part of a monocarboxylic acid amide" is here understood that said amide constitutes at least 50% by weight of the amide product mixture. The secondary amine, which is one of the reactants in the process, has a catalytic effect and it seems to catalyse rather selectively its own alkoxylation. The presence of an effective amount of an alkoxylation catalyst other than the secondary amine must be avoided, as this will favour undesired side reactions.

DESCRIPTION OF THE PREFERRED EMBODIMENTS

By the method of this invention, the contents of secondary amines are reduced to less than 1% by weight, while the undesired side reactions, such as alkoxylation of hydroxyl groups and esterification, are kept on a low level. Furthermore, the amide product mixture obtained is a clear, homogeneous fluid at room temperature, although the starting amide product mixture is normally solid or semi-solid. In order to further suppress the side reactions it has been found suitable to perform the reaction below 100° C., preferably below 80° C., and most perferably below 60° C. The amount of alkylene oxide added has to be adjusted according to the amount of secondary amines, so that the latter can be alkoxylated to the corresponding tertiary alkanol amine. Normally, the molar ratio of alkylene oxide to the secondary amine is 1.0 to 1.25, perferably 1.01–1.15.

Suitable monocarboxylic acid amides with the formula (I) are those, where the acyl group RCO is derived from fatty acid or aliphatic saturated or unsaturated, straight or branched synthetic acids. Specific examples of such monocarboxylic acids are 2-ethylhexanoic acid, n-octanoic acid, pelargonic acid, iso-nonanoic acid, n-decanoic acid, lauric acid, myristic acid, palmitic acid and oleic acid.

The choice of carboxylic acids regulates, among other things, the HLB-value of the monocarboxylic acid amides, but also the choice of the secondary amine is of importance. Normally, groups $R_1$ and $R_2$ designate groups containing few carbon atoms, but in case group R has a low number of carbon atoms and/or a rather hydrophobic amide is desired, it may be advantageous to elect secondary amines with alkyl or hydroxy-alkyl groups with more than 4 carbon atoms. The same is valid also for the choice of alkylene oxide. However, normally $R_1$ and $R_2$ designate lower alkyl groups, such as methyl, ethyl, propyl, isopropyl, butyl or isobutyl; or hydroxyalkyl, such as hydroxyethyl, hydroxypropyl and hydroxybutyl. Examples of suitable secondary amines with formula (II) are methylhydroxyethylamine, ethylhydroxyethylamine, methylhydroxypropylamine and ethylhydroxypropylamine. Especially diethanolamine and diisopropanolamine are preferred.

The choice of alkylene oxide affects the HLB-value of the tertiary alkanolamine formed during the reaction and a higher alkylene oxide may be preferred if a tertiary alkanolamine with a more hydrophobic and surface active character is desired. Normally, the alkylene oxide used has 2–4 carbon atoms. Although ethylene oxide reacts easily with the secondary amine, it has surprisingly been found that propylene oxide and higher alkylene oxides react with a high selectivity with respect to the hydrogen atom bound to the nitrogen atom in the secondary amine resulting in a low degree of side reactions like propoxylation of hydroxyl groups in the secondary or tertiary amine or in esterification.

The amide product mixture according to the invention which is obtainable by the above described process and contains a minor amount of a tertiary alkanolamine has very advantageous properties. Thus, application tests have clearly indicated that the amide product mixture according to the invention is very suitable to be used as a component in cosmetic formulations, such as shampoos and creams; foam cleaning compositions, e.g. for textiles and cars; and aqueous functional fluids, such as lubricants, metal working fluids and hydraulic fluids. The contents of tertiary amines in the amide product mixture contribute to improved corrosion inhibiting and foaming properties. When the amide product mixture is used in aqueous functional fluids, the monocarboxylic acid amide with Formula (I) is normally based on a monocarboxylic acid containing 14–22 carbon atoms, while when used in cosmetic formulations and foam cleaning compositions, monocarboxylic acid amides based on carboxylic acids having 8–13 carbon atoms are normally preferred.

The present invention is further illustrated by the following examples.

EXAMPLES 1–2

An amide product mixture containing about 92% by weight of the compound $RCON(C_2H_4OH)_2$, where RCO is derived from coconut fatty acid, and 5.8% by weight of diethanolamine was used as a starting material. The amide product mixture was obtained by reacting the methyl ester of coconut fatty acid with diethanolamine. An amount of 950 g of the amide product mixture was added to a pressure reactor, whereupon 26.2 g of ethylene oxide or 33 g of propylene oxide was added gradually and an alkoxylation reaction took place at a controlled temperature of 55° C. in the absence of any alkoxylation catalyst. After complete reaction the reaction mixture was cooled and analysed. The content of the diethanolamine found in the reaction mixture was determined at less than 0.5% by weight (ethoxylation) and less than 0.3% by weight (propoxylation) respectively.

The content of the carboxylic acid amide compound was in both cases about 89.5%, which indicates that undesired esterification reactions are kept on a low level.

EXAMPLES 3–4

The amide product mixtures obtained in Examples 1–2 were tested with respect to their effects on iron corrosion in accordance with Institute of Petroleum, IP 287, Corrosion Test. The product mixtures were dissolved in amounts of 1, 2, or 3% by weight in soft water (1,2° dH) and the pH value was adjusted with diluted acetic acid to 9.9. The following results were obtained.

TABLE 1

| Amide mixture | Corrosion, % of area stained Addition | | | |
|---|---|---|---|---|
| | 0% | 1% | 2% | 3% |
| Unalkoxylated | 100 | 45 | 45 | 25 |
| Ethoxylated | 100 | 25 | 15 | 8 |
| Propoxylated | 100 | 45 | 15 | 8 |

From the results it is evident that the alkoxylated amide containing products according to the invention have superior corrosion inhibition properties in comparison with the unalkoxylated reference.

EXAMPLE 5

The ethoxylated amide product mixture according to Example 1 was dissolved in an amount of 25 mg together with 250 mg of sodium lauryl sulphate into 200 g of water having a total hardness of 10° dH or 20° dH. The pH value was adjusted to 7. The foaming ability of the formulations was then evaluated in accordance with Institute of Petroleum, IP 312, Foam Test. The following results were obtained.

TABLE 2

| Water hardness | Temperature | Foam height, cm Amide product | |
|---|---|---|---|
| °dH | °C. | Unalkoxylated | Ethoxylated |
| 20 | 30 | 400 | 430 |
|  | 40 | 435 | 460 |
| 10 | 30 | 415 | 450 |
|  | 40 | 440 | 490 |

From the results it is evident that the product according to the invention is able to advantageously replace the conventional unalkoxylated amide product mixtures in cosmetics and foam cleaning compositions.

EXAMPLES 6 TO 8

An amide product mixture containing about 71% by weight of the compound $RCON(C_2H_4OH)_2$, where RCO is derived from a 1:1 mixture by weight of $C_{16}$ and $C_{18}$ fatty acids and about 25% by weight of diethanolamine was used as a starting material. The amide mixture was obtained by reacting the fatty acid mixture with diethanolamine.

An amount of 818 g of the amide product mixture was added to a pressure reactor followed by the gradual addition of 100 g ethylene oxide, 130 g propylene oxide or 159 g butylene oxide, whereupon alkoxylation was carried out in the absence of any alkoxylation catalyst at 60° C. After complete reaction, the product mixture was cooled and analysed. The content of diethanolamine was determined to less than 0.9% (ethoxylation), 0.6% (propoxylation), and 0.6% (butoxylation).

EXAMPLES 9–11

Semi-synthetic cutting fluid concentrates were formulated from the following ingredients.

TABLE 3

| Material | Fluid A | Fluid B | Fluid C |
| --- | --- | --- | --- |
| Monoethanolamine | 4.0 | 4.0 | 4.0 |
| Triethanolamine | 9.0 | 9.0 | 9.0 |
| Boric acid | 6.0 | 6.0 | 6.0 |
| Water | 16.0 | 16.0 | 16.0 |
| Alkylene glycol | 3.0 | 3.0 | 3.0 |
| Water soluble dispersant | 1.5 | 1.5 | 1.5 |
| Copper inhibitor | 0.2 | 0.2 | 0.2 |
| Paraffinic mineral oil | 37.5 | 37.5 | 37.5 |
| Tall oil fatty acid (distilled) | 7.2 | 7.2 | 7.2 |
| Ethoxylated groundnut fatty amide mixture | 12.0 | — | — |
| Propoxylated groundnut fatty amide mixture | — | 12.0 | — |
| Butoxylated groundnut fatty amide mixture | — | — | 12.0 |
| Alcohol type coupler | 3.6 | 3.6 | 3.6 |

The concentrates were then diluted with water in accordance with Table 3 and then tested with respect to corrosion and foaming in the same manner as in Examples 3 and 5 respectively. The following results were obtained.

TABLE 4

| | Corrosion, % of area stained Dilution ratio | | | | |
| --- | --- | --- | --- | --- | --- |
| Fluid | 1:20 | 1:30 | 1:40 | 1:50 | 1:60 |
| A | 0 | 0 | 3 | 30 | 40 |
| B | 0 | 0 | 5 | 20 | 40 |
| C | 0 | 0 | 3 | 25 | 40 |

TABLE 5

| | Foam height, cm Seconds | | | | | |
| --- | --- | --- | --- | --- | --- | --- |
| Fluid | 0 | 15 | 30 | 60 | 90 | 180 |
| A | 90 | 40 | 20 | 10 | 5 | 0 |
| B | 85 | 65 | 40 | 20 | 5 | 0 |
| C | 85 | 65 | 30 | 15 | 5 | 0 |

The results indicate that it is possible to formulate cutting fluids with good corrosion inhibiting effects and low initial foam heights which collapse quickly upon resting.

EXAMPLE 12

Example 1 was repeated, but 1.016 g of an amide product mixture containing 67% by weight of $RCON(C_2H_4OH)_2$, where RCO was derived from groundnut fatty acid, and 29% by weight of diethanolamine was used as the starting material. The addition of ethylene oxide was 135 g. After ethoxylation, the diethanolamine content was less than 0.6% by weight.

EXAMPLE 13

Metal working fluids of the microemulsion type were prepared in accordance with the formulations below.

TABLE 6

| | % by weight | |
| --- | --- | --- |
| Material | Fluid D | Fluid E |
| Paraffinic mineral oil | 53.95 | 53.95 |
| Sodium petroleum sulphonates | 17.5 | 17.5 |
| Tall oil fatty acids (distilled) | 10.0 | 10.0 |
| Groundnut fatty diethanol amide mixture[1] | 6.0 | — |
| Ethoxylated groundnut fatty amide mixture[2] | — | 6.0 |
| Potassium hydroxide (50%) | 4.6 | 4.6 |
| Triethanolamine | 1.0 | 1.0 |
| Calcium petroleum sulphonates | 0.45 | 0.45 |
| Biocide | 0.65 | 0.65 |
| Glycol ether coupling agent | 3.85 | 3.85 |
| Copper inhibitor solution | 2.0 | 2.0 |

[1] Starting material in Example 12.
[2] According to Example 12.

The formulations were tested in 200 ppm (as $CaCO_3$) hard water with regard to their ability to prevent iron corrosion in the manner described in Example 3 and their foaming were determined in accordance with the VSI Foam Test procedure. The following results were obtained.

TABLE 7

| | % Area of filter paper stained | |
| --- | --- | --- |
| Dilution | Fluid D | Fluid E |
| 40:1 | 1 | 1 |
| 50:1 | 10 | 5 |
| 60:1 | 13 | 8 |
| 80:1 | 30 | 12 |

TABLE 8

| | | Foam developm. (secs) Probe | | | | Foam decay (secs) Probe | | |
| --- | --- | --- | --- | --- | --- | --- | --- | --- |
| Fluid | Conc. | 1 5 cms | 2 10 cms | 3 15 cms | Delay (secs) | 3 15 cms | 2 10 cms | 1 5 cms |
| D | 3% | 2.4 | 24.0 | 127.2 | 40 | 2.3 | 9.3 | 68.0 |
| E | 3% | 2.8 | 27.2 | 136.5 | 40 | 1.9 | 8.2 | 64.6 |

Note
Pressure 1.5 bar
Probe heights 5, 10, 15 cms above fluid surface

From the test results it is evident that the formulation containing the ethoxylated amide product mixture (fluid E) is superior in comparison with the formulation containing the unethoxylated amide product mixture.

What is claimed is:

1. A method of producing an amide product mixture containing at least 50% by weight of a carboxylic acid amide and less than 1% by weight of a secondary amine, comprising:

(a) providing a product mixture comprised of:
   at least 50% by weight, based on the product mixture, of a carboxylic acid amide having a formula

   (I)

where R is an aliphatic hydrocarbon group having 7–23 carbon atoms, $R_1$ and $R_2$ are, independently of each other, an alkyl group having 1–8 carbon atoms or a hydroxyalkyl group having 2–8 carbon atoms, and more than 1% by weight, based on the product mixture, of a secondary amine having a formula

   (II)

where $R_1$ and $R_2$ are, independently of each other, an alkyl group having 1–8 carbon atoms or a hydroxyalkyl group having 2–8 carbon atoms; and (b) alkoxylating the product mixture by reaction thereof with an aliphatic alkylene oxide having 2–8 carbon atoms in the absence of any alkoxylation catalyst until the content of the secondary amine in the product mixture is less than 1% by weight to provide the amide product mixture containing at least 50% by weight of a carboxylic acid amide and less than 1% by weight of a secondary amine, wherein alkoxylation produces alkoxylation of the secondary amine to a corresponding tertiary amine while the carboxylic acid amide present in the product mixture is essentially not alkoxylated.

2. The method according to claim 1, wherein the secondary amine is diethanolamine.

3. The method according to claim 1, wherein the alkylene oxide is selected from the group consisting of ethylene oxide and propylene oxide.

4. The method according to claim 1, further comprising preparing the carboxylic acid amide by reacting a substance selected from the group consisting of a carboxylic acid having the formula RCOOH, where R is an aliphatic hydrocarbon group having 7–23 carbon atoms, a salt thereof, and an alkylester thereof, with the secondary amine having the formula (II).

5. The method according to claim 4, wherein the alkylester is a methyl ester.

6. A process according to any one of the claim 1 which is carried out at a temperature below 100° C.

7. The method according to claim 1, wherein alkoxylating the reaction product is carried out at a temperature below 80° C.

8. The method according to claim 1, wherein alkoxylating the reaction product is carried out at a temperature below 60° C.

* * * * *